United States Patent
Wood et al.

(10) Patent No.: US 10,251,711 B2
(45) Date of Patent: Apr. 9, 2019

(54) OPTICAL PROBES FOR CORRIDOR SURGERY

(71) Applicants: Michael Frank Gunter Wood, Toronto (CA); Cameron Anthony Piron, Toronto (CA)

(72) Inventors: Michael Frank Gunter Wood, Toronto (CA); Cameron Anthony Piron, Toronto (CA)

( * ) Notice: Subject to any disclaimer, the term of this patent is extended or adjusted under 35 U.S.C. 154(b) by 0 days.

(21) Appl. No.: 15/523,731

(22) PCT Filed: Jan. 7, 2015

(86) PCT No.: PCT/CA2015/000012
§ 371 (c)(1),
(2) Date: May 2, 2017

(87) PCT Pub. No.: WO2016/109887
PCT Pub. Date: Jul. 14, 2016

(65) Prior Publication Data
US 2018/0071030 A1 Mar. 15, 2018

(51) Int. Cl.
*A61B 6/00* (2006.01)
*A61B 34/20* (2016.01)
(Continued)

(52) U.S. Cl.
CPC .......... *A61B 34/20* (2016.02); *A61B 1/00154* (2013.01); *A61B 1/00188* (2013.01);
(Continued)

(58) Field of Classification Search
CPC ..... A61B 34/20; A61B 5/0062; A61B 5/0059; A61B 5/0075; A61B 90/30;
(Continued)

(56) References Cited

U.S. PATENT DOCUMENTS

| | | |
|---|---|---|
| 6,591,049 B2 | 7/2003 | Williams et al. |
| 7,488,468 B1 | 2/2009 | Miwa et al. |

(Continued)

OTHER PUBLICATIONS

International Search Report dated Sep. 18, 2015 for International Application No. PCT/CA2015/000012.
(Continued)

*Primary Examiner* — Amelie R Gillman
(74) *Attorney, Agent, or Firm* — Perry + Currier Inc.

(57) ABSTRACT

Optical probes for port-based corridor surgery are provided, including a device comprising: a surgical tool mounting adaptor configured for mounting to a surgical tool; an optical probe attached to the surgical tool mounting adaptor, the optical probe comprising: an optical interface end; an optical output end, distal the optical interface end, the optical output end comprising illumination optics and collection optics, the illumination optics configured to illuminate tissue proximal the optical output end, the collection optics configured to collect an optical signal from the tissue; one or more illumination optical fibers configured to convey illumination light from the optical interface end to the illumination optics; and, one or more collection optical fibers configured to convey the optical signal collected by the collection optics to the optical interface end.

14 Claims, 7 Drawing Sheets

(51) Int. Cl.
*A61B 1/00* (2006.01)
*A61B 5/00* (2006.01)
*A61B 90/30* (2016.01)
*A61B 90/50* (2016.01)
*A61B 90/57* (2016.01)
*A61B 1/07* (2006.01)
*A61B 17/3201* (2006.01)
*A61B 1/018* (2006.01)
*A61B 5/055* (2006.01)
*A61B 17/32* (2006.01)
*A61B 17/34* (2006.01)
*A61B 17/00* (2006.01)
*A61B 90/00* (2016.01)

(52) U.S. Cl.
CPC ............ *A61B 1/00195* (2013.01); *A61B 1/07* (2013.01); *A61B 5/0059* (2013.01); *A61B 5/0062* (2013.01); *A61B 5/0066* (2013.01); *A61B 5/0075* (2013.01); *A61B 5/0084* (2013.01); *A61B 5/4523* (2013.01); *A61B 17/3201* (2013.01); *A61B 90/30* (2016.02); *A61B 90/36* (2016.02); *A61B 90/50* (2016.02); *A61B 90/57* (2016.02); *A61B 1/018* (2013.01); *A61B 5/0086* (2013.01); *A61B 5/0095* (2013.01); *A61B 5/055* (2013.01); *A61B 5/4233* (2013.01); *A61B 5/4504* (2013.01); *A61B 5/4519* (2013.01); *A61B 5/4533* (2013.01); *A61B 5/489* (2013.01); *A61B 5/4893* (2013.01); *A61B 17/320068* (2013.01); *A61B 17/3423* (2013.01); *A61B 2017/00477* (2013.01); *A61B 2034/2055* (2016.02); *A61B 2090/306* (2016.02); *A61B 2090/3614* (2016.02); *A61B 2090/373* (2016.02); *A61B 2090/3735* (2016.02); *A61B 2505/05* (2013.01)

(58) Field of Classification Search
CPC ... A61B 1/00188; A61B 1/00195; A61B 1/07; A61B 17/3201; A61B 2090/306; A61B 5/055; A61B 2017/00477; A61B 5/4523; A61B 5/4533; A61B 2034/2055; A61B 5/0066; A61B 2505/05
See application file for complete search history.

(56) References Cited

U.S. PATENT DOCUMENTS

| | | | | |
|---|---|---|---|---|
| 2002/0009275 | A1* | 1/2002 | Williams | G02B 6/0008 385/123 |
| 2009/0281536 | A1* | 11/2009 | Beckman | A61B 5/0059 606/33 |
| 2010/0198080 | A1* | 8/2010 | Liu | A61B 5/0071 600/477 |
| 2010/0234684 | A1* | 9/2010 | Blume | A61B 1/00165 600/104 |
| 2011/0015648 | A1* | 1/2011 | Alvarez | A61B 17/221 606/130 |
| 2011/0040172 | A1* | 2/2011 | Carpentier | A61B 5/0068 600/411 |
| 2012/0116209 | A1 | 5/2012 | Klee et al. | |
| 2013/0317355 | A1* | 11/2013 | Jacobsen | A61B 5/062 600/424 |
| 2014/0005489 | A1* | 1/2014 | Charles | A61B 17/02 600/214 |
| 2014/0075721 | A1* | 3/2014 | Denmark | B25G 1/10 16/421 |

OTHER PUBLICATIONS

Written Opinion dated Sep. 18, 2015 for International Application No. PCT/CA2015/000012.

* cited by examiner

OPTICAL PROBES FOR CORRIDOR SURGERY

FIELD

The specification relates generally to surgical instruments, and specifically to optical probes for corridor surgery.

BACKGROUND

Probes for optical measurements of tissue may provide a wide variety of applications and modalities, for providing clinicians with details regarding the state of tissue to guide diagnosis, treatments and/or surgery. The optical modalities for which probes have been developed include broadband spectroscopy (ultraviolet, visible, near infrared, and short wave infrared), fluorescence, Raman spectroscopy, optical coherence tomography, photoacoustic tomography, coherence anti-Stokes Raman spectroscopy, confocal microscopy, among others.

Port-based surgery is a minimally invasive surgical technique where a port (generally a cylindrical plastic tube open on both ends) is introduced to access the surgical region of interest. Unlike other minimally invasive techniques, such as laparoscopic techniques, the port diameter is larger than the tool diameter, allowing bi-manual tool manipulation within the port. Hence, the tissue region of interest is accessible through the port. While a wide variety of optical probes have been developed for numerous modalities, optical probes for port-based surgery have not been developed. For example, current optical probes are not compatible with port-based surgery due to sizes of the probe, sterilization tolerance, lack of signal enhancing mechanisms, lack of integration with surgical tools, lack of position and orientation tracking, and lack integration with other optical systems. At present the lack of these features hinders and restricts the use and utility of optical probes for port-based surgery. Similar respective restrictions may also exist with other types of surgical techniques.

SUMMARY

The present specification provides an optical probe which is attachable to a surgical instrument, and specifically, a device that includes an optical probe which may be used for port surgery, and other types of surgeries. The optical probe may be used for a variety of optical modalities including, but not limited to: ultraviolet (UV), visible (VIS), near infrared (NIR), and shortwave infrared (SWIR) broadband spectroscopy; Raman spectroscopy; fluorescence; both spectral domain and swept source optical coherence tomography (OCT), photoacoustic tomography, laser induced breakdown spectroscopy (LIBS), surface enhanced Raman spectroscopy (SERS), coherent anti-Stokes Raman spectroscopy (CARS), stimulate Raman scattering (SRS), probe-based microscopy, probe-based confocal microscopy, and the like. The probe may be adapted to include signal enhancing materials, nanoparticles, and the like, that may be affixed to the end of the probe to provide enhancement of an optical signal overall and/or to conjugate with specific biological molecules of interest and emit a molecular specific signal. The probe may be adapted to track a position thereof as part of a surgical navigation system. As positions of the probes are tracked, and the location of the measurements is known, and methods to relate a volume from which the optical signal originated to pixels or voxels from other imaging modalities may be utilized.

The probe may include a single optical fiber or collection of optical fibers that delivers illumination light to tissue, including, but not limited to, through a port (e.g., broadband UV, VIS, NIR, and/or SWIR; laser; Raman excitation laser; OCT broadband or swept source light; photoacoustic excitation; fluorescence excitation; LIBS excitation, etc.), as well as A single optical or collection of optical fibers that collect an optical signal from tissue being accessed (e.g. through a port), including, but not limited to, light reflected from the tissue. These optical fibers may have a variety of arrangements; for example, the optical fibers may be arranged in a circular fashion with illumination light fiber(s) in the centre and collection light fiber(s) arranged around the illumination fiber(s). Optical lenses or lenslets may be used to control the solid angle of illumination and collection, as well as for focussing or collimation of either the illumination or collection light.

The probe is generally inserted into a patient, for example through the surgical port, and placed in contact or short stand-off from the tissue to provide tissue characterization and differentiation, to assist in surgical decision making by providing an indication of tissue status. For example, a surgeon would identify a region of tissue on which they wish to perform a measurement, bring the probe into contact or short stand-off from the tissue, and measure the optical signal. The measured signal may be processed at a light analyzer, and the like, and displayed as part of a surgical visualization system.

A size and/or geometry of the probe is controlled and/or configured to enable insertion of the probe into a port. For example, the probe may have be cylindrical and have a diameter of less than or equal to about 5 mm, and a length of greater than or equal to about 5 cm.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, ZZ, and the like). Similar logic may be applied for two or more items in any occurrence of "at least one . . . " and "one or more . . . " language.

An aspect of the present specification provides a device comprising: a surgical tool mounting adaptor configured for mounting to a surgical tool; an optical probe attached to the surgical tool mounting adaptor, the optical probe comprising: an optical interface end; an optical output end, distal the optical interface end, the optical output end comprising illumination optics and collection optics, the illumination optics configured to illuminate tissue proximal the optical output end, the collection optics configured to collect an optical signal from the tissue; one or more illumination optical fibers configured to convey illumination light from the optical interface end to the illumination optics; and, one or more collection optical fibers configured to convey the optical signal collected by the collection optics to the optical interface end.

The surgical tool mounting adaptor may be further configured for removable attachment to the surgical tool.

The surgical tool mounting adaptor may comprise a sleeve configured for removable attachment to the surgical tool.

The surgical tool mounting adaptor may be further configured to hold the optical probe in a fixed position relative to the surgical tool.

The surgical tool mounting adaptor may be configured for mounting to one or more of: a suction device, scissors, microscissors, a bipolar surgical tool, a drill, a resection device, a shaving device, a forceps, an ultrasonic cutting device, and an aspirator.

The device may further comprise a mount configured to removably attach the optical probe to the surgical tool mounting adaptor.

The optical probe may comprise a sleeve and a rigid optical probe portion, the sleeve configured to removably hold the rigid optical probe portion. The sleeve may be one or more of sterilizable and consumable, the sleeve may be further configured to seal the rigid optical probe portion from the tissue. The optical output end may be integrated into the sleeve, and the rigid optical probe portion may comprise the one or more illumination optical fibers and the one or more collection optical fibers. The rigid optical probe portion may be sealed.

The optical probe may be cylindrical, a diameter of the optical probe is less than or equal to about 5 mm, and a length of a rigid portion of the optical probe is greater than or equal to about 5 cm.

The optical interface end may comprise a connector configured to: connect the one or more illumination optical fibers to an illuminator configured to provide the illumination light; and connect the one or more collection optical fibers to a light analyzer configured to receive and analyze the optical signal from the one or more collection optical fibers.

The optical output end may further comprise a shield configured to one or more of: contact the tissue; and maintain a standoff distance between the tissue and one or more of the illumination optics and the collection optics.

The illumination optics and the collection optics may comprise one or more of a lens, a mirror, and a prism.

One or more of the illumination optics and the collection optics may comprise at least one of electromechanical components and MEMS (micro-electromechanical systems) components to move optical components.

The illumination optics and the collection optics may be configured to vary one or more of: a focal point, a depth of the focal point in the tissue, an illumination spot size, a voxel of the tissue, a numerical aperture of the collection optics, a direction of the illumination light, and a direction of the optical signal collected from the tissue.

The optical output end may comprise one or more materials configured to one or more of: enhance the optical signal from the tissue; and, provide one or more of a molecular, protein, and cellular binding-specific signal. The materials may comprise one or more of: signal enhancing materials, bio-conjugation specific materials, binding materials, antibodies, arrays, microarrays, assays, and hollow-core photonic crystal fibers.

The device may further comprise a mount configured to removably attach a tracking device to one or more of the surgical tool mounting adaptor and the optical probe.

The device may further comprise a mount configured to removably attach a tracking device of a surgical navigation system to one or more of the surgical tool mounting adaptor and the optical probe.

BRIEF DESCRIPTIONS OF THE DRAWINGS

For a better understanding of the various implementations described herein and to show more clearly how they may be carried into effect, reference will now be made, by way of example only, to the accompanying drawings in which.

DETAILED DESCRIPTION

The OCT (optical coherence tomography) technique described herein may be used to specifically visualize tissue exhibiting structural organization. Examples of such tissue structures include tendons that are attached to bones. Other examples of tissue that exhibit structural organization include ligaments, muscle, cartilage, tissue connective membrane, nerves, retina, blood vessel walls, some bone structures, trachea, esophagus, tongue and teeth.

Polarization Sensitive-OCT (PS-OCT) is a subset of OCT that detects different polarizations of light reflected from the sample. OCT in general does not necessary detect the intensity from the different polarization of light, but rather detects the intensity of randomly polarized light. PS-OCT commonly generates a heat map or pseudo colored image (reference: "Correlation of collagen organization with polarization sensitive imaging of in vitro cartilage: implications for osteoarthritis," W. Drexler et. al, The Journal of Rheumatology, Vol. 28, No. 6, 1311-1318) where tissue structures with high degree of organization appear highlighted. This system may be used in orthopedic surgery to visualize tendons and optionally avoid unintentional damage to this tissue during a procedure. These identified regions of tissue exhibiting high level of structural organization (e.g. tendons and ligaments that are often located near skeletal structure) may be used in conjunction with a priori information, such as known points of attachment of tendons to bones, to geometrically correlate PS OCT images to CT and MR images where bones are easily imaged.

The insertion sites, tendon-bone junctions and ligament-bone junctions, are known as entheses. The anatomical locations of entheses are well known and landmarks may be identified on the bone in the vicinity of these attachment points (reference: "Anatomy and biochemistry of enthuses," Michael Benjamin, Ann Rheum Dis 2000, Vol. 59, Issue 12, pg: 995-999). Hence, this a priori anatomical information about the position of the tendon or ligament relative to bone structures in the vicinity may be used to register intraoperative PS-OCT image of the tendons or ligaments with pre-operative images obtained using other modalities that accurately image the bone structures.

For example the tendon-bone junction in the Achilles tendon enthesis is immediately proximal to the superior tuberosity. This region is characterized by a highly irregular interface at the attachment points or junction. This characteristic structure of the bone may be used to identify the junction where the tendon attaches to the bone. The geometric correlation of images that are thus obtained using different modalities, and often at different scales, is known as image registration or image fusion.

Common methods for multi-modal image registration mentioned above include those described in "Multi-modal image registration for pre-operative planning and image guided neurosurgical procedures," Risholm, et. al, Neurosurg Clin N Am, 2011, April; 22(2): 197-206 and "Image registration of ex-vivo MRI to sparsely sectioned histology of hippocampal and neocortical temporal lobe speciments," Goubran et. al, NeuroImage, 83 (2013); 770-781. Broad classes of image registration methods for medical images is also described in detail in "A survey of medical image registration," Maintz et. al, Medical Image Analysis (1998), Vol. 2, No. 1, pp: 1-36.

Figure 1:
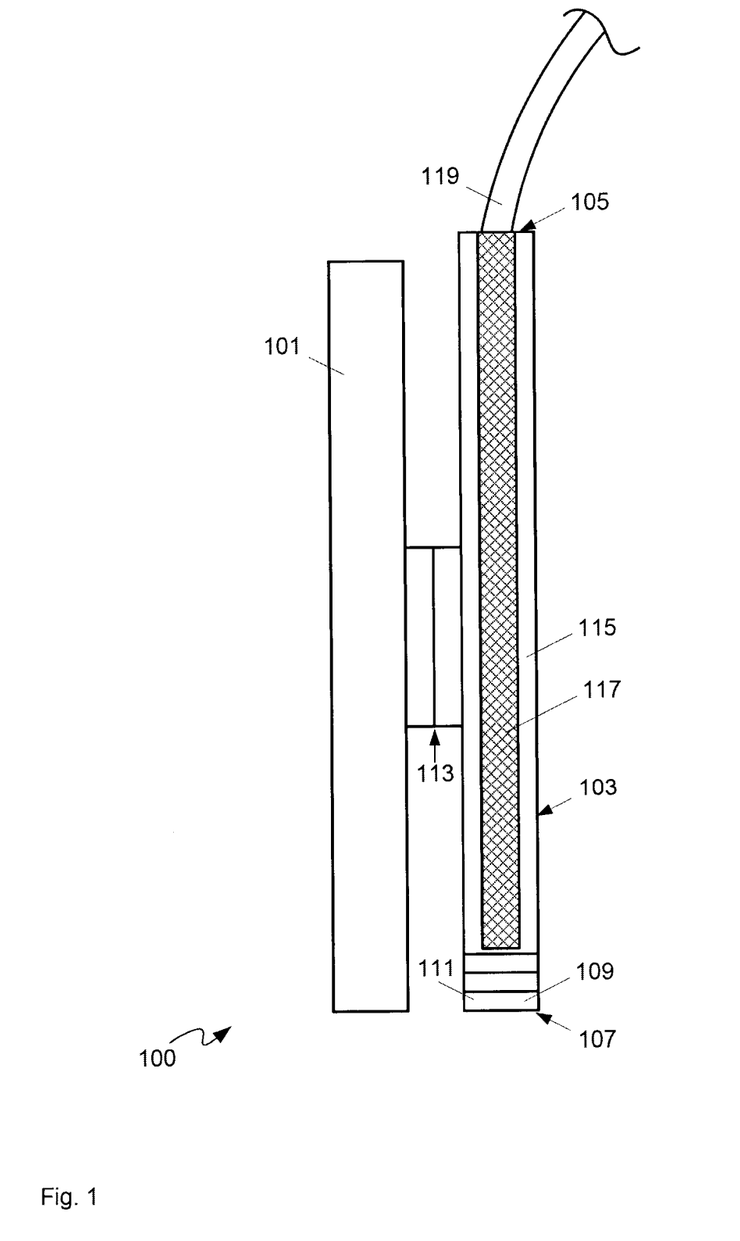
FIG. 1 depicts a device that includes an optical probe for corridor surgery, according to non-limiting implementations.

Attention is directed to FIG. 1 which depicts a schematic diagram of a device 100 comprising: a surgical tool mounting adaptor 101 configured for mounting to a surgical tool; an optical probe 103 attached to surgical tool mounting adaptor 101, optical probe 103 comprising: an optical interface end 105; an optical output end 107, distal optical interface end 105, optical output end 107 comprising illumination optics 109 and collection optics 111, illumination optics 109 configured to illuminate tissue proximal optical output end 107, collection optics 111 configured to collect an optical signal from the tissue; one or more illumination optical fibers (not visible in FIG. 1) configured to convey illumination light from optical interface end 105 to illumination optics 109; and, one or more collection optical fibers (not visible in FIG. 1) configured to convey the optical signal collected by collection optics 111 to optical interface end 105. Surgical tool mounting adaptor 101 will be interchangeably referred to hereafter as adaptor 101. One or more illumination optical fibers will be interchangeably referred to hereafter as illumination optical fibers; and one or more collection optical fibers will be interchangeably referred to hereafter as collection optical fibers.

As depicted, device 100 further comprises a mount 113 configured to removably attach optical probe 103 to adaptor 101.

Furthermore, as depicted, device 100 further comprises a sleeve 115 and a rigid optical probe portion 117, sleeve 115 configured to removably hold rigid optical probe portion 117. In FIG. 1, sleeve 115 is depicted as transparent to show rigid optical probe portion 117 inside, however, sleeve 115 may be opaque and the optical properties of sleeve 115 are generally non-limiting, other than optical properties of optical output end 107. Indeed, as depicted, optical output end 107 is integrated into sleeve 115, and rigid optical probe portion 117 comprises the one or more illumination optical fibers and the one or more collection optical fibers. However, optical probe 103 may extend beyond sleeve 115 and rigid optical probe portion 117; for example, optical fibers of optical probe 103 may extend from optical interface end 105.

In other implementations, device 100 could comprise a flexible device where the direction and angle of bend may be controlled by tension members attached to a wall of optical probe 103. The tension members could be actuated mechanically or could be made of memory metal alloys (e.g. including, but not limited to, Nitinol) that is actuated electrically.

As depicted, mount 113 may comprise a first portion connected to adaptor 101 and a second portion connected to optical probe 103 and/or sleeve 115, the first portion and the second portion configured to attach to one another. Mount 113 may hence comprise a magnetic mount, a slot and groove connector, respective clips, and the like. However, in other implementations, mount 113 may comprise a clip, and the like, attached to adaptor 101 configured to hold optical probe 103 and/or sleeve 115; conversely, in yet further implementations, mount 113 may comprise a clip, and the like, attached to optical probe 103 and/or sleeve 115 configured to hold adaptor 101.

As depicted, optical interface end 105 comprises a connector 119 configured to: connect the one or more illumination optical fibers to an illuminator configured to provide the illumination light; and connect the one or more collection optical fibers to a light analyzer configured to receive and analyze the optical signal from the one or more collection optical fibers. As depicted, connector 119 is located at optical interface end 105 and/or at an end of rigid optical probe portion 117; however, in other implementations, connector 119 may be located anywhere along optical fibers extending from rigid optical probe portion 117. While details of connector 119 are not depicted, connector 119 may comprise an optical fiber connector, and the like.

Figure 2:
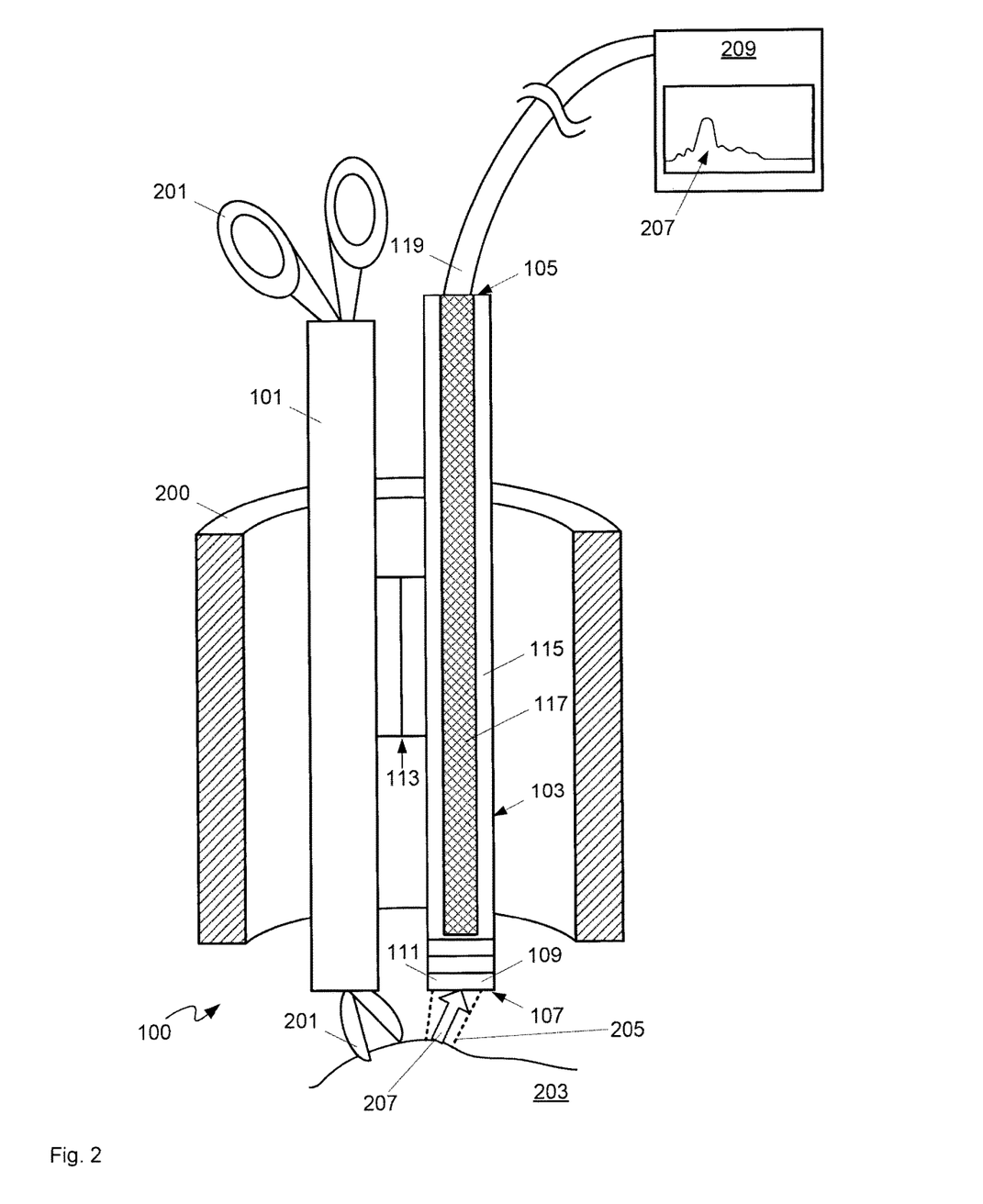
FIG. 2 depicts the device of FIG. 1, in use, according to non-limiting implementations.

Attention is next directed to FIG. 2, which is substantially to FIG. 1, with like elements having like numbers, and depicts a schematic diagram of device 100 in use with a surgical port 200, which is depicted schematically in cross-section, and a surgical tool 201 to interact with tissue 203 through port 200. However, while present implementations are described with reference to port-based corridor surgery, device 100 may be used with other types of corridor and/or invasive and/or non-invasive surgeries. FIG. 2 further depicts illumination light 205 from illumination optics 109 illuminating a portion of tissue 203 with which surgical tool 201 is interacting, and an optical signal 207 collected from tissue 203 by collection optics 111 conveyed to a light analyzer 209 where optical signal 207 is visually provided, for example as a function of wavelength. While not depicted, it is assumed that the system depicted in FIG. 2 further comprises an illuminator configured to provide illumination light 205, the illuminator connected to illumination optical fibers using connector 119. Hence, connector 119 is configured to: connect the illumination optical fibers to the illuminator configured to provide illumination light 205; and connect the collection optical fibers to light analyzer 209 configured to receive and analyze optical signal 207 from the collection optical fibers.

Specifically, in FIG. 2, adaptor 101 is mounted to surgical tool 201, a handle (e.g. a handle of a scissors) of surgical tool 201 depicted as protruding from a first end of adaptor 101 and a tissue interaction end (e.g. blades of the scissors) of surgical tool 201 protruding from a second end of adaptor 101, distal the first end. Hence, it is apparent that, in depicted implementations, adaptor 101 comprises a sleeve configured for removable attachment to a surgical tool 201. While surgical tool is depicted as a scissors, surgical tool mounting adaptor 101 may be configured for mounting to one or more of: a suction device, a scissors, a microscissors, a bipolar surgical tool, a drill, a resection device, a shaving device, a forceps, an ultrasonic cutting device, and an aspirator. While adaptor 101 is depicted as a sleeve, adaptor 101 may comprise other devices for mounting optical probe 103 to a surgical tool including, but not limited to, mechanical clamps, magnetic clamps, and the like, with or without a sleeve. It is further appreciated that, while not depicted, adaptor 101 comprises one or more devices for fixing a position of adaptor 101 on surgical tool 201, including, but not limited to, a clamp. In general, adaptor 101 is further configured for removable attachment to surgical tool 201

From FIG. 2, it is apparent that a diameter of optical probe 103 is less than an inner diameter of port 200, and further that a length of a rigid portion of optical probe 103 is greater than a length of port 200. Surgical ports may have inner diameter of 13.5 mm and lengths of 5, 6, and 7.5 cm, however, ports of other diameters and lengths are possible. In some implementations, a diameter of optical probe 103 is no more than about ⅓ a diameter of a port with which optical probe 103 is to be used. In specific non-limiting implementations, optical probe 103 is cylindrical, a diameter of the optical probe is less than or equal to about 5 mm, and a length of the optical probe is greater than or equal to about 5 cm. However, optical probe 103 may be adapted for use with surgical ports of different diameters and different lengths; hence, for example, when a surgical port of 7.5 cm is to be used, a rigid portion of optical probe 103 may be greater than or equal to 7.5 cm. Indeed, different optical probes of different lengths (and/or different diameters and/or different geometries) may be provided, each adapted for use with a given surgical port.

It is further apparent from FIG. 2 adaptor 101 is further configured to hold optical probe 103 in a fixed position relative thereto and/or relative to surgical tool 201. For example, adaptor 101 may be rigid, at least when attached to surgical tool 201, and adaptor 101 may be configured to hold optical probe 103 such that optical output end 107 is proximal and/or adjacent a tissue interaction end of surgical tool 201 and/or such that illumination light 205 is illuminating an area proximal a tissue interaction end of surgical tool 201. Hence, optical signal 207 is always received from a portion of tissue 203 that is interacting with, and/or being acted on, and/or being cut by, surgical tool 201. And, as the tissue interaction end of surgical tool 201 moves, optical output end 107 of optical probe 103 moves in a similar fashion.

Such relative motion may be further translated from adaptor 101 to optical probe 103 using mount 113, which may be rigid and/or hold optical probe 103 in a fixed position relative thereto and/or relative to surgical tool 201.

It is furthermore appreciated that the sizes and geometry of components of FIGS. 1 and 2 are not to scale. Hence, while in FIG. 2, illumination light 205 is depicted as being steered to the left (relative to a tissue interaction of surgical tool 201), such steering is depicted to illustrate that illumination light 205 is illuminating an area proximal a tissue interaction end of surgical tool 201, and such steering may or may not occur depending on optical components of illumination optics 109 and collection optics 111, and/or a position of the tissue interaction end of surgical tool 201. For example, a geometry and/or size of adaptor 101 and optical probe 103 (and/or mount 113) may be adapted so that illumination light 205 illuminates an area of tissue 203 that is proximal the tissue interaction end of surgical tool 201 without changing a direction of illumination light 205.

From FIGS. 1 and 2, it is apparent that, as depicted, sleeve 115 holds rigid optical probe portion 117 therein such that an end of rigid optical probe portion 117 distal optical interface end 105 interacts with optical output end 107 integrated into sleeve 115. In some of these implementations, rigid optical probe portion 117 may be removable from sleeve 115 such that sleeve 115 and/or rigid optical probe portion 117 may be modular with other sleeves and/or other rigid optical probes. Specifically, sleeve 115 may be removed from rigid optical probe portion 117, and optically further detached from adaptor 101, and sterilized separately there from.

Alternatively sleeve 115 may be consumable, so that sleeve 115 may be replaced each time surgery occurs and thrown away thereafter. In some of these implementations, illumination optics 109 and collection optics 111 may be integrated with rigid optical probe portion 117 so that illumination optics 109 and collection optics 111 are not disposed of after each surgery; in these implementations, an end of sleeve 115 comprises a window so that illumination light 205 and optical signal 207 may pass through window.

In these implementations, rigid optical probe portion 117 may be sealed for easy sterilization and/or so that sterilization of rigid optical probe portion 117 need not be as thorough as sterilization of sleeve 115, which is in contact with, and/or adjacent to, tissue 203, and further shields rigid optical probe portion 117 from tissue 203.

In some implementations where sleeve 115 is consumable (and/or disposable), system 100 may comprise a standoff configured to offset optical output end 107 a given distance from tissue 203, the given distance selected for imaging tissue 203 using one or more given optical modalities. Furthermore, in other implementations where sleeve 115 is consumable, the non-consumable (i.e. non-disposable) portions of system 100 may be placed flushed with the consumable portions of system 100, to facilitate cleaning thereof.

Figure 3:
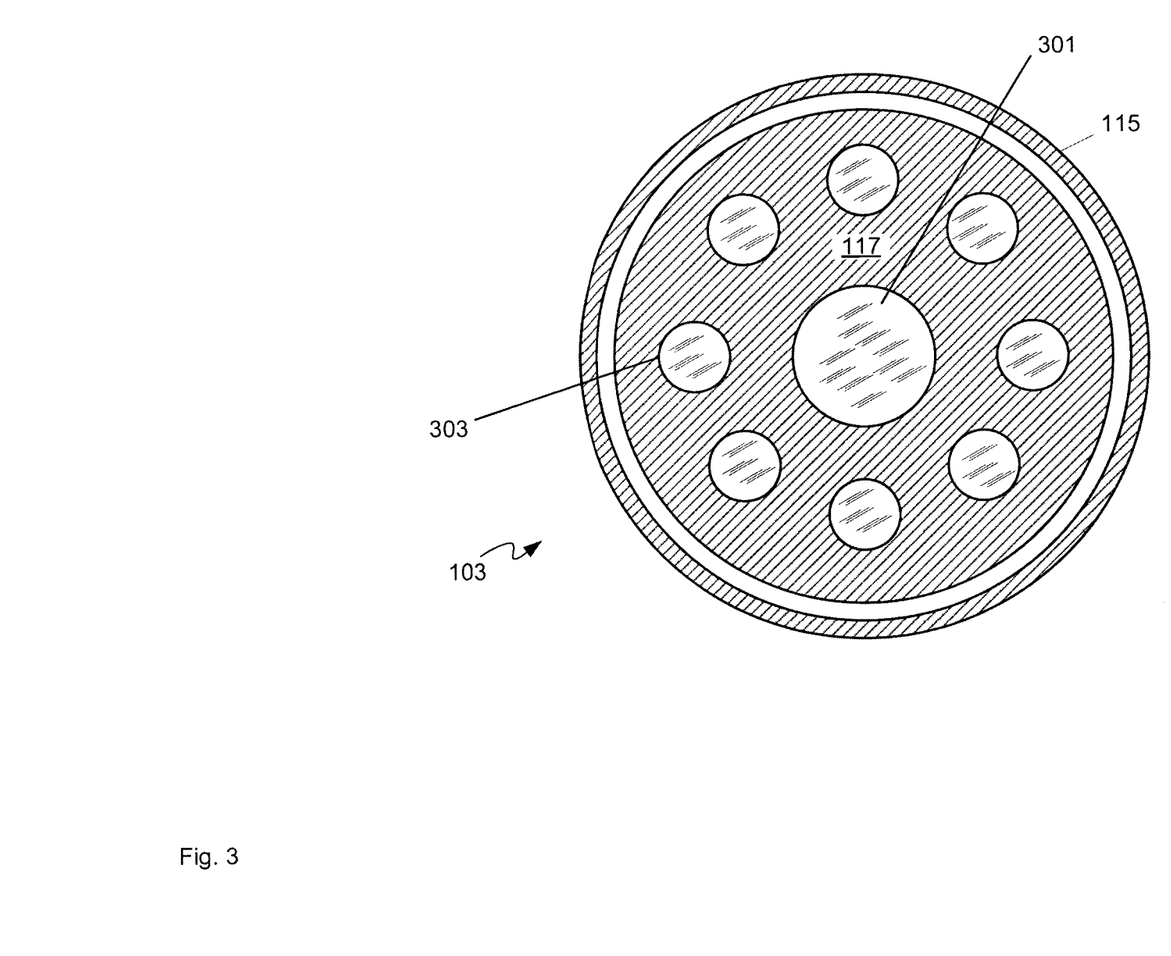
FIG. 3 depicts a cross-section of the optical probe, according to non-limiting implementations.

Attention is next directed to FIG. 3, which depicts a lateral cross-section of optical probe 103, which is depicted as cylindrical, though optical probe 103 may be of other geometries. Sleeve 115 and rigid optical probe portion 117 are hence depicted in cross-section, and illumination optical fiber(s) 301, and collection optical fiber(s) 303 are depicted in cross-section in rigid optical probe portion 117. For clarity only one collection optical fiber 303 is indicated, though, eight collection optical fibers 303 are shown. One or more of illumination optical fiber(s) 301 and collection optical fiber(s) may comprise a single optical fiber and/or a fiber optic bundle. As depicted, illumination optical fiber(s) 301 comprises one or more optical fibers running along about a centre of rigid optical probe portion 117, while collection optical fiber(s) 303 are arranged circularly around illumination optical fiber(s) 301. However, other arrangements are within the scope of the present specification as long as illumination optical fiber(s) 301 convey illumination light 205 to optical output end 107 and collection optical fiber(s) 303 convey optical signal 207 from optical output end 107 to optical interface end 105.

In some implementations, optical output end 107 may be adapted to include a shield and/or a spacer. For example, attention is next directed to FIG. 4, which depicts a non-limiting implementation of optical output end 107 of optical probe 103, optical output end 107 adapted to comprise a shield 401 configured to one or more of: contact tissue 203; and maintain a standoff distance between tissue 203 and one or more of illumination optics 109 and collection optics 111. In other words, shield 401 may comprise a spacer of a that maintains a distance between tissue 203 and one or more of illumination optics 109 and collection optics 111, that corresponds to a length of shield 401, presuming an end of shield 401 is in contact with and/or proximal to tissue 203. At least the end of shield 401 in contact with and/or proximal to tissue 203 hence comprises a window, an aperture and the like and/or is generally configured for illumination light 205 and/or optical signal 207 to pass therethrough. For example, a length of shield 401 may be adapted for a given size of a spot and/or focal length of illumination light 205.

Figure 4:
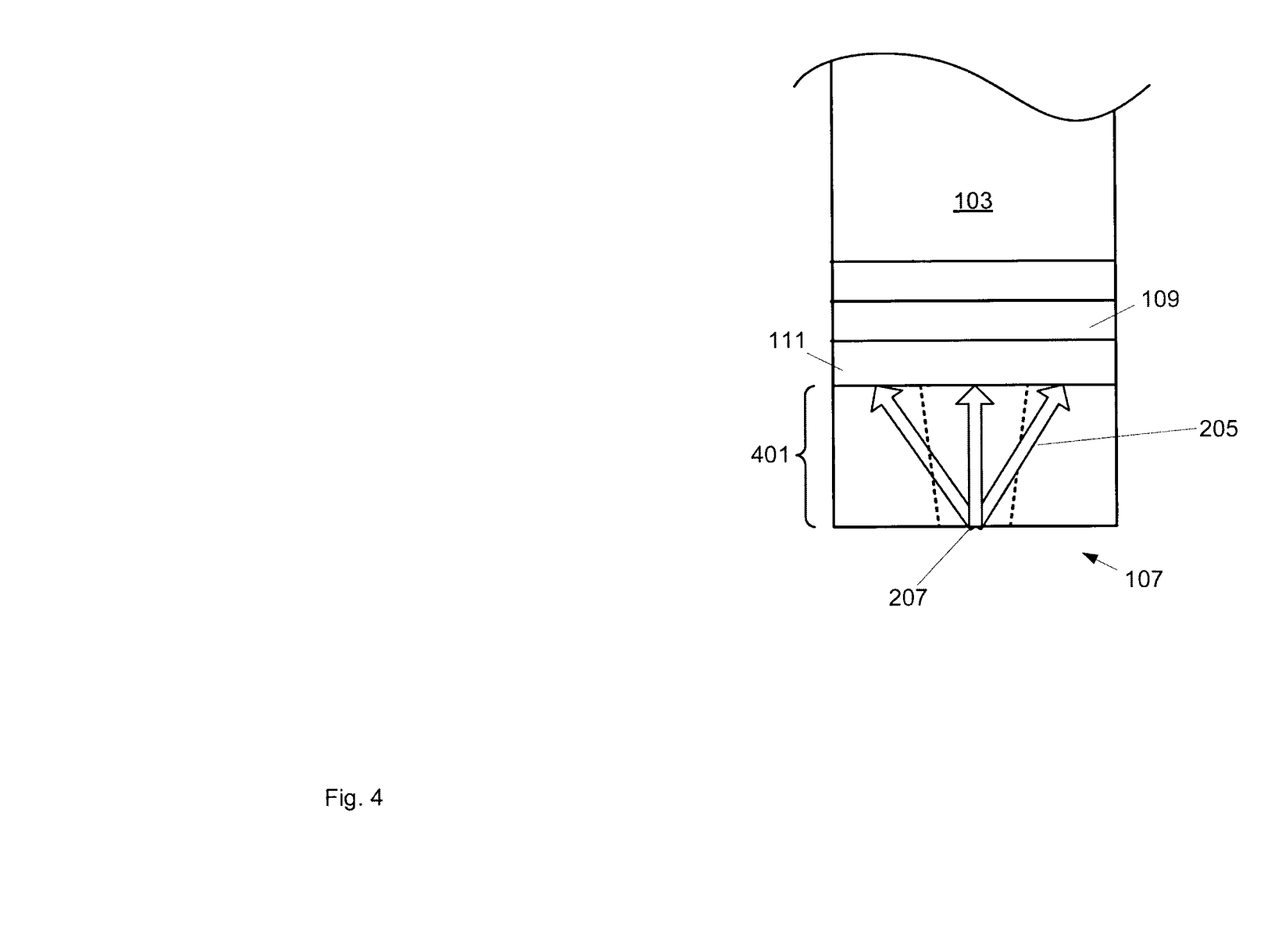
FIG. 4 depicts an optical probe adapted with a shield, according to non-limiting implementations.

In some implementations, shield 401 may be configured to absorb laser light; for example when illumination light comprises laser light, shield 401 may protect a user from exposure to laser light, by absorbing such, to assist in preventing eye damage. In yet further implementations, system 100 may be adapted to include one or more sensors configured to sense that laser light is imaging and/or irradiating tissue 203 and/or system 100 may be configured to determine when laser light is imaging and/or irradiating tissue 203. For example, in some implementations, tissue 203 may be probed using OCT before and/or interleaved with imaging tissue 203 using other optical modalities; in further implementations, a position of optical probe 103 may be tracked relative to a patient, for example using a position tracking system as described below with reference to FIG. 7, and laser light light is activated only when optical probe 103 is determined to be inside a patient. Alternatively, a laser is prevented from being activated unless at least optical output end 107 is inside of the patient.

Figure 5:
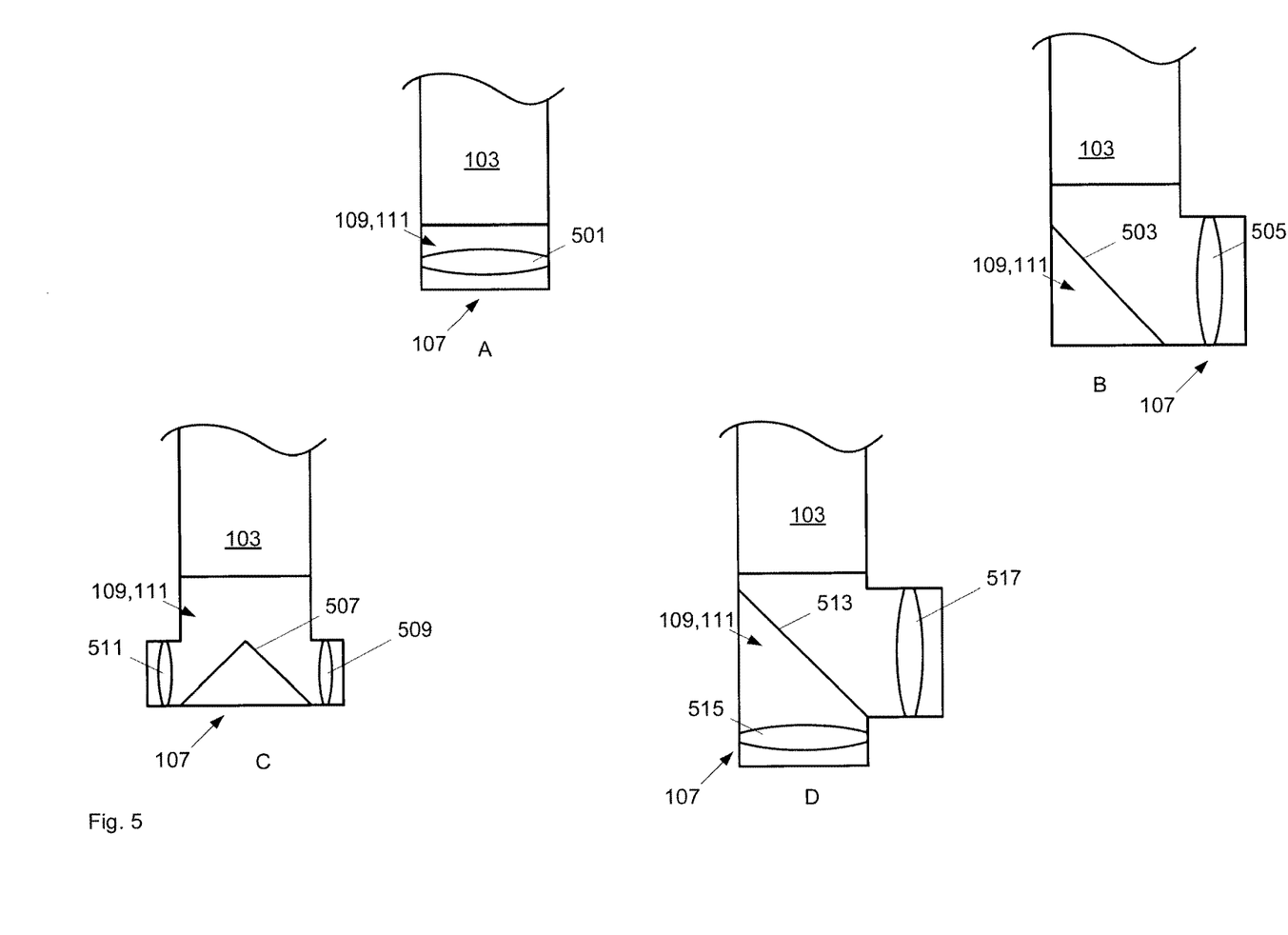
FIG. 5 depicts various illumination and collection optics of the optical probe, according to non-limiting implementations.

Attention is next directed to FIG. 5, which depicts various implementations of illumination optics 109 and collection optics 111 of optical output end 107 of optical probe 103. Indeed, illumination optics 109 and collection optics 111 comprise one or more of each of lenses, lenslets, minors, dichroic mirrors, conical minors, prisms, and the like, and/or combinations thereof. Furthermore, illumination optics 109 and collection optics 111 may be combined into one set of optics that both conveys illumination light 205 to tissue 203 and collects optical signal 207.

In any event, in implementation "A", illumination optics 109 and collection optics 111, comprise one or more lenses 501 (including, but not limited to lens systems, lenslets and the like) configured to focus illumination light 205 from illumination optical fibers 301 along a cylindrical and/or longitudinal axis of optical probe 103, and collect and convey optical signal 207 to collection optical fibers 303.

In contrast, in implementation "B", illumination optics 109 and collection optics 111, comprise a mirror 503 configured to reflect illumination light 205 from illumination optical fibers 301 by about 90° relative to a cylindrical and/or longitudinal axis of optical probe 103 through a lens 505 similar to lens 501, but located along a lateral axis of optical probe 103. Hence, illumination light 205 illuminates an area along the lateral axis of optical probe 103, and optical signal 207 is collected from the same area. Such implementations may be used with surgical tools that interact with tissue 203 at a 90° angle.

Implementation "C" is similar to implementation "B", however a minor 507 splits illumination light 205 into two portions, a first portion conveyed 90° towards a first lens 509 in a first lateral direction, and a second portion conveyed 90° towards a second lens 511 in a second lateral direction, which may be 180° from first lateral direction (as depicted) or another lateral direction. Hence, two areas of tissue 203 are illuminated by illumination light 205, and optical signal 207 is collected from the two areas. Such implementations may be used with surgical tools that interact with tissue 203 in two areas at 90° angles.

Implementation "D" is similar to implementation "B", however a dichroic mirror 513 splits illumination light 205 into two portions, a first portion conveyed towards a first lens 515 in a first direction along a cylindrical and/or longitudinal axis of optical probe 103, and a second portion conveyed 90° towards a second lens 517 in a second direction, 90° from the first direction (as depicted) or another direction. Hence, two areas of tissue 203 are illuminated by illumination light 205, and optical signal 207 is collected from the two areas. Such implementations may be used with surgical tools that interact with tissue 203 in two areas at a 0° angle and a 90° angle.

In some implementations, optical probe 103 may be adapted to include multiple heads that may be used one or more microscope type compound lenses, and optionally with different optical filters.

While FIG. 5 depicts optical components that direct illumination light 205 by 0° and/or 90°, and optionally splits illumination light 205 into two portions, other optical components that direct illumination light 205 by other angles and/or into more than two portions are within the scope of the present specification. For example, optical end 107 may be adapted for a given surgical tool to direct illumination light 205 in one or more directions in accordance with a geometry of the given surgical tool. Furthermore, when sleeve 115 is interchangeable, a plurality of sleeves may be provided with different optics to adapt device 100 for given surgical tools.

Furthermore, optical probe 103 may be adapted to deliver different types of illumination light 205 in different directions and/or to different areas of tissue 203, for example each type of illumination light associated with different optical modalities. In a particular non-limiting example, optical probe 103 may include optical devices that may deliver light used in fluorescence-based modalities on one side of optical probe 103 and, and light used in Raman-based modalities on another side of optical probe.

In some implementations, system 100 may include quantum dots as an illumination source, which may be external to optical probe 103, with light there from delivered to optical output end 107 using optical fibres and/or such quantum dots may be incorporated at optical output end 107, with optical probe 103 including a connection to a an external power source to power the quantum dots.

Furthermore, one or more of illumination optics 109 and collection optics 111 may comprise at least one of electromechanical components and MEMS (micro-electromechanical systems) components to move optical components. For example, such components may be used to steer and/or change an angle of illumination light 205. Similarly, one or more of illumination optics 109 and collection optics 111 may be configured to vary one or more of: a focal point, a depth of the focal point in tissue 203, an illumination spot size, a voxel of tissue 203, a numerical aperture of the collection optics, a direction of illumination light 205, and a direction of optical signal 207 collected from tissue 203. For example, electromechanical components and MEMS (micro-electromechanical systems) components may be used to move components of illumination optics 109 and collection optics 111 to adjust interaction of illumination light 205 with tissue 203.

In yet further implementations, optical output end 107 may comprise one or more materials configured to one or more of: enhance optical signal 207 from tissue 203; and, provide one or more of a molecular, protein, and cellular binding-specific signal. In other words, optical output end 107 may be coated and/or treated with materials that interact with tissue 203 to enhance a signal emitted from tissue 203. In particular non-limiting implementations, optical nose technology may be combined with optical probes described herein.

Figure 6:
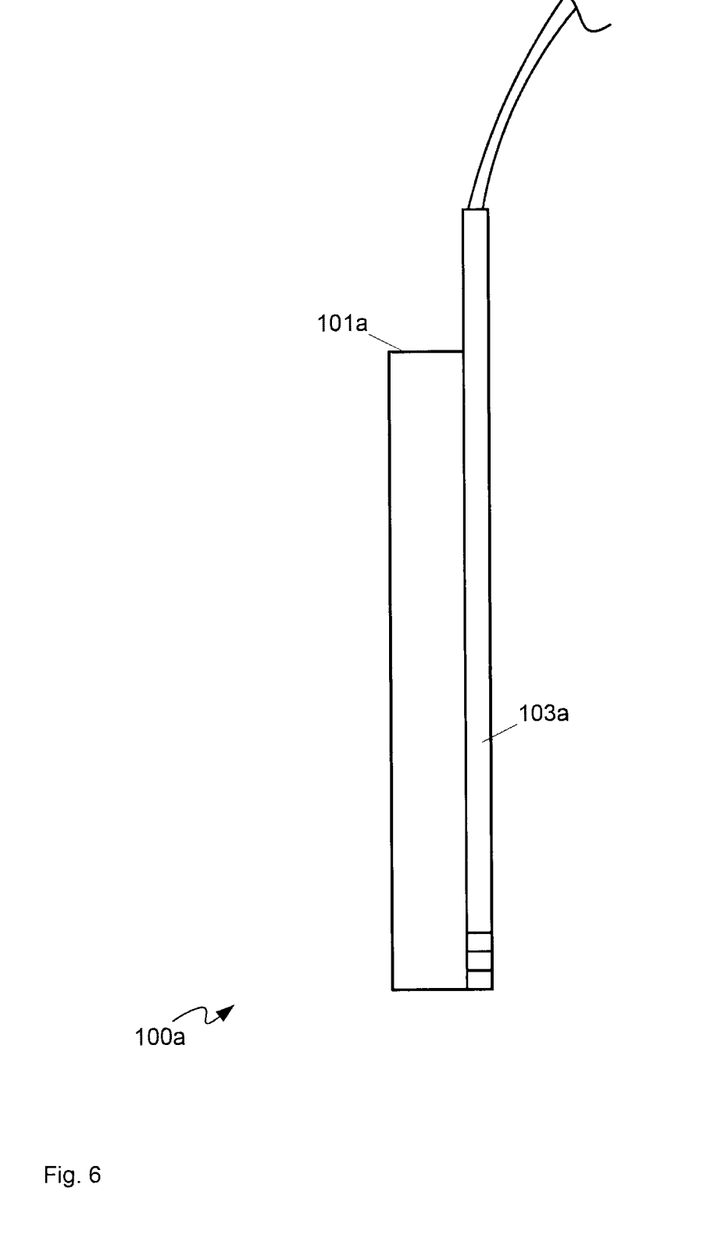
FIG. 6 depicts an alternative device that includes an optical probe for corridor surgery, according to non-limiting implementations.

Persons skilled in the art will appreciate that there are yet more alternative implementations and modifications possible. For example, attention is directed to FIG. 6, which depicts an alternative device 100*a*, which is substantially similar to device 100, device 100*a* comprising an adaptor 101*a*, similar to adaptor 101, and an optical probe 103*a*, which is functionally similar to optical probe 103. While not all components of device 100*a* are shown and/or numbered, device 100*a* is nonetheless similar to device 100 except that optical probe 103*a* is integrated with adaptor 101*a*, and is not removable there from. Indeed, as depicted optical probe 103*a* does not comprise a sleeve and a separate rigid optical probe portion contained therein; rather, as depicted, optical probe 103*a* has illumination optical fibers, collection optical fibers and an optical output end integrated into one piece attached to adaptor 101*a*. However, in other implementations, optical probe 103*a* may have a structure similar to optical probe 103, with sleeve attached to adaptor 101*a*, and a removable rigid optical probe portion.

Figure 7:
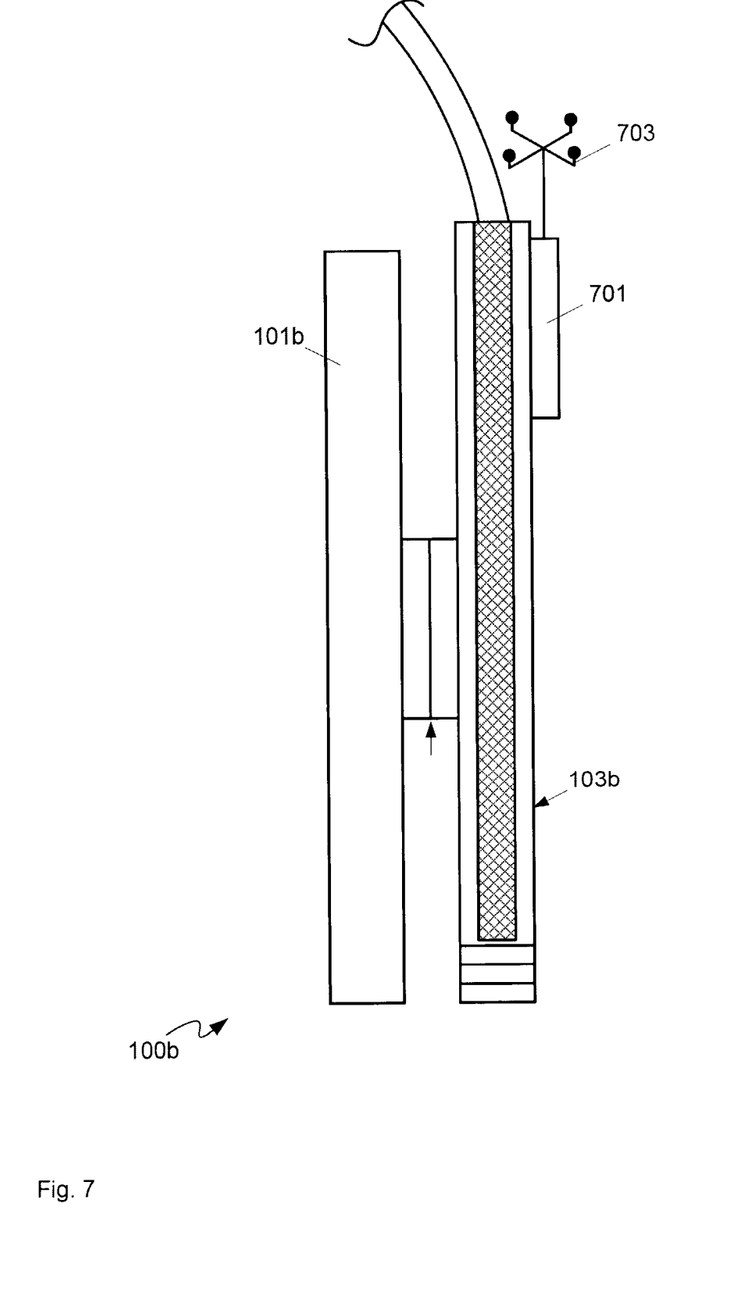
FIG. 7 depicts an alternative device that includes an optical probe for corridor surgery and a mount for receiving a tracking device used with surgical navigational system, according to non-limiting implementations.

Attention is next directed to FIG. 7 which depicts an alternative device 100*b*, which is substantially similar to device 100, device 100*b* comprising an adaptor 101*b*, similar to adaptor 101, and an optical probe 103*b*, similar to optical probe 103. While not all components of device 100*b* are shown and/or numbered, device 100*a* is nonetheless similar to device 100. However, device 100*b* further comprises a mount 701 configured to removably attach a tracking device 703 of a surgical navigation system to one or more of surgical tool mounting adaptor 101*b* and optical probe 103*b* (including, but not limited to, a sleeve of optical probe 103*b*). While as depicted mount 701 is attached to optical probe 103*b*, in other implementations, mount 701 may be attached to adaptor 101*b*. Mount 701 generally comprises a mount for receive an end of device 703 so that tracking elements of device 703 extend away from one or more of an optical interface end and a surgical port with which device 100*b* is being used, so that a camera, and the like, of a surgical navigation system may track a position of device 703 and hence a position of probe 103*b* in the surgical port. As depicted, tracking device 703 comprises four reflective spheres arranged in a configuration where each sphere is located at about a corner of a square. However, other numbers of spheres and other configurations are within the scope of present implementations. In particular or more of a number, arrangement, and configuration of such spheres may be selected to provide a given tracking accuracy, including, but not limited to, a tracking accuracy that is less than about half a diameter of a sensing array surface.

However, tracking device 703 may include tracking devices other than reflective spheres. For example, in some implementations, tracking device 703 may include a flexible sheath configured to measure tip position deflection, for example deflection of a tip of the flexible sheath.

Hence, disclosed herein are contact optical probes for use in corridor surgery, for example port-based corridor surgery. Various geometries and sizes of the optical probes may be used with various surgical ports and may be mounted to a surgical tool using a surgical tool mounting adaptor. A sleeve, and the like, may be used to seal at least a portion of the probe from the outside environment. The probe may be adapted for to mount a tracking device. As the probe is tracked, and the location of the measurements are known, and a volume from which an optical signal originated may be related with pixels and/or voxels from other imaging modalities. Hence, probe measurements may be collected using an attached analyzer, and the measurements may also be input into other measurement or imaging datasets.

In yet further implementations, contact optical probes may be adapted for use with catheters rather than ports for corridor surgery. For example, one or more of a size, length, diameter and configuration of contact optical probes described herein may be adapted for use with a catheter.

Furthermore, optics may be provided to change the focus, collimation and/or direction of illumination light and collection of a resulting optical signal.

In general the probe: may be used inside of a surgical port; provides good ergonomics for use in a surgical port; provides a "universal" probe holder to attach to various surgical tools; allows attachment of tracking devices which allows a position of the probe to be tracked in a surgical navigation system; and may be sealed so as to not contact tissue. In some implementations, interrogation and collection volumes may be varied. Further, signal enhancing mechanisms and/or specific conjugation agents may be applied to an end of the probe that is to contact tissue. Signal enhancing materials, nanoparticles, etc. to be affixed to the end of the probe to provide enhancement of the overall signal and/or to conjugate with specific biological molecules of interest and emit a molecular specific signal.

Optical probes described herein may be used for a variety of optical modalities including, but not limited to: ultraviolet (UV), visible (VIS), near infrared (NIR), and shortwave infrared (SWIR) broadband spectroscopy; Raman spectroscopy; fluorescence; both spectral domain and swept source optical coherence tomography (OCT), photoacoustic tomography, laser induced breakdown spectroscopy (LIBS), surface enhanced Raman spectroscopy (SERS), coherent anti-Stokes Raman spectroscopy (CARS), stimulate Raman scattering (SRS), probe-based microscopy, probe-based confocal microscopy, and the like.

In yet further implementations, optical probes described herein may be adapted to include one or more devices for sampling tissue that is provided to a mass spectrometer such that mass spectrometry of tissue may be combined with a variety optical modalities for characterizing the sampled tissue, in order to differentiate between different tissue types. For example, with reference to FIG. 2, tissue 203 from which optical signal 207 is received may be sampled using surgical tool 201, and the like, and collected using a suitable device (e.g. a tube, and the like, and associated suction device) that transports the sampled tissue to a mass spectrometer. Hence, a sample of tissue 203 from which optical signal 207 is received may also be characterized using mass spectrometry. In other words, a common sensing pathway may be used with both mass spectrometry and one or more optical modalities to differentiate between different tissue types. In some implementations, a mass spectrometer sampling device may be incorporated into optical probe 103, while in other implementations, a mass spectrometer sampling device may be provided through port 200 in addition to optical probe 103 and mounting adaptor 101. Furthermore, an intake of the mass spectrometer sampling device is about proximal to optical output end 107 of optical probe 103. In some implementations such a mass spectrometer sampling device may be mounted to one or more of optical probe 103 and mounting adaptor so that that an intake of the mass spectrometer sampling device is about proximal to optical output end 107 of optical probe 103. In some of these implementations, optical probe 103 may be adapted to include an aperture in optical output end 107. Hence, for example, optical output end 107 may a generally transparent window for optical imaging, the aperture may be connected to a passage in optical probe 103 that is in turn in communication with both a vacuum for sampling tissue 203 and a mass spectrometry device In yet further implementations, system 100 may be adapted for irrigation flush a face of optical output end 107 during surgery such that tissue contamination of optical output end 107 and/or any apertures in a mass spectrometer sampling device may be reduced.

The general form of the probe is a single optical fiber or collection of optical fibers that deliver illumination light to tissue (e.g., broadband UV, VIS, NIR, and/or SWIR; laser; Raman excitation laser; OCT broadband or swept source light; photoacoustic excitation; fluorescence excitation; LIBS excitation, etc.) and a single optical fiber or collection of optical fibers that collect light reflected from the tissue. These fibers may have a variety of arrangements; in some implementations, they are arranged in a circular fashion with illumination light fiber(s) in the centre and collection light fiber(s) arranged around the illumination fiber(s). Optical lenses or lenslets may be used to control a solid angle of illumination and collection, as well as for focussing or collimation of either the illumination or collection light.

In some implementations, systems described herein may be configured to interrogate a tissue state based on "a priori" information and/or other imaging system information. Informatics, and the like, may be used in such implementations. For example, an initial probe and/or image of tissue 203 may be obtained and analyzed, and further probing of tissue 203 may be performed based on the initial probe and/or image.

The probe is inserted into a surgical port and placed in contact or short stand-off from tissue, with a wide variety of potential optical modality specific probes. The probe provides for tissue characterization and differentiation, to assist in surgical decisions making by providing an indication of tissue status. For example, a surgeon could identify a region of tissue on which they wish to perform a measurement, bring the probe into contact or short stand-off from the tissue, and measure the optical signal. The measured signal could be processed and displayed as part of an overall surgical visualization system; processing of the optical signal may occur to display the optical signal in a format that is readily interpretable by the surgeon.

In order for the probe to be inserted into a surgical port, a diameter of the probe is adapted to be less than and/or significantly less than the diameter of the port such that the surgeon may easily visualize the tissue at the bottom of the port while the probe is in the field-of-view and easily maneuver the probe within the port. As bi-manual tool manipulation is an important advantage, in general, of port systems, the probe may be adapted to be small enough that another tool may be present in the port at the same time. Surgical ports presently used have an inside diameter of 13.5 mm and lengths of 5, 6, and 7.5 cm, however, ports of other diameters and lengths are possible. Given the inner diameter of a port, a probe diameter of about ⅓ the inner diameter of the surgical port may be used so that tissue visualization at the bottom of the port occurs, provide ease of manoeuvring of the probe, and allow for additional tools to be present in the port. From a mechanical standpoint, as the probe may be in contact with living tissue, the probe may be adapted to be sealed, sterile, and re-sterilizable and/or consumable. As an alternative to the probe being sterile or sterilizable, the probe could be sealed inside a sterile sleeve during surgery, and the sleeve could either be re-sterilizable or consumable. This sleeve would remove some of the sterility requirements on the probe itself, thus relaxing some of the manufacturing constraints with regards to producing a sterile end product.

A number of features may be incorporated in the probe to assist with the ergonomics of use inside the surgical port. For example, the a portion of the probe that is to be located inside the port may be rigid with a length greater than the length of the port, with enough length beyond the port to allow the surgeon to easily grasp the rigid portion of the probe, and easily maneuver the probe within the port. For example, such a rigid portion may comprise a rigid metal tube containing the illumination and collection fibers. This rigid portion that extends beyond the top of the port is useful for manoeuvring and/or positioning fiber optics within the port. However, other implementations, the probe could comprise a flexible device where the direction and angle of bend may be controlled by tension members attached to the wall of the probe. The tension members could be actuated mechanically or could be made of memory metal alloys (e.g. including, but not limited to, Nitinol) that is actuated electrically.

Furthermore, the probe may include a shield around an optical output/tissue end so that the tip of this shield may come into contact with tissue of interest and maintain an optimal stand-off distance for the probe optics to illuminate and collect light from the tissue. This also allows for ease of positioning of the probe during use. The shield also has the benefit of blocking ambient light from being collected by the probe. The front of the shield may either be left open via an aperture or sealed with a window; sealing the shield has the benefit of keeping the excitation and collection optics of the probe away from the tissue (ease of sterilization and cleaning) as well as better maintaining the optimal stand-off distance from the tissue than a hollow opening, as tissue may deform and bulge when under contact pressure.

The optical output/tissue end of the probe may include optics to vary a focal point and/or size and/or area of illumination and collection to allow for variation of the illumination spot size (changing depth of the focal point) and/or changing the numerical aperture of the collection optics. This may be accomplished through movement of optics (including, but not limited to lens groups), and/or other components that may modify the refractive index and/or shape of the optics, such that the spot size of illumination and/or numerical aperture of collection optics are modified. This change in the illumination spot size and/or the numerical aperture of collection changes the volume of interaction and collection respectively. The ability to modify these volumes allows for optical measurements to be collected from a controllable approximate volume of tissue. The integration or collection volume as function of illumination spot size and collection numerical aperture may be calculated through various analytical methods such as diffusion theory or statistical methods including, but not limited to Monte Carlo modelling of light propagation in scattering. Using these methods a lookup table of both integration and collection volumes as function of illumination spot size and collection numerical aperture, respectively, may be constructed. These lookup tables could be used to tune to an approximated desired interrogation or collection volume; the known interrogation and collection volumes may then be controlled to relate the optical measurements to pixels or voxels from other imaging modalities, for example MRI, CT, Ultrasound, PET, SPECT, OCT, photoacoustics, etc., as part of an overall multimodality multi-resolutional operating room imaging system.

In addition, mirrors, beam splitters, and other reflective optical elements may be placed at the output/tissue end of the probe to modify the direction, shape, or other parameters of the illumination and/or collection beam, including, but not limited to: mirrors to redirect the illumination and collection beams to various geometries; conical mirrors to distribute an input parallel beam into a radial angularly distributed beam; and beam splitters to divide an input beam into two or more beams in perpendicular directions.

Instead of adapting various probes for specific uses (i.e., tool mounted, varying illumination/detection geometries, mounting tracking devices, etc.), a "universal" probe holder with standard housing, attachments, and optics may be utilized. The holder may be specific to a model of probe, however, the attachments, mounts, and optics may be modular. The general form of the probe may be a cylindrical sleeve that grasps, holds, and/or covers the probe, with an opening for light illumination and collection at optical output/tissue end of the probe. The opening of the probe holder may have an optical window to seal the probe from the outside environment, with window materials including, but not limited to, sapphire, quartz, etc. This optical window may also provide the standoff distance from the probe optics to the tissue, allowing a user to place the probe in contact with the tissue of interest while ensuring that the tissue of interest is at an optimal distance from the receiver optics in the probe. Optimality of placement may be defined as presenting the expected tissue area (or volume) of interest to the sensing modality in the probe. The probe holder could contain optics to change the direction (i.e., aiming) of the excitation and collection light paths, as described above, to be optimal for the specific use of the probe, for example forward viewing, side viewing, various other angles, etc. These optics could include one or more mirrors to change the direction of the beams as well as lenses to alter to focus and accordingly the optimal stand-off from the tissue for both illumination and collection; the optical assembly could also include electromechanical components and/or MEMS components to move optics (e.g. lens sets) in order to modify the focus and accordingly the volume of integration. The optics of the probe holder hence may be adapted for a specific use (direction, focus, collimation, shape, etc.), as opposed to producing probes for each specific use. As, in these implementations, the probe is contained within the holder, the sterility constraints on the probe itself may be relaxed if the probe holder is sealed and prevents the probe from coming into direct contact with the tissue. In this case, only the probe holder and not the probe itself would require complete sterilization; this potentially avoids wear and tear on the probe from the sterilization process (in particular on the seals, joints, adhesives, optical surfaces, coatings applied to optics etc.). The probe holder could alternatively be a consumable item that ships sterile and is disposed of after a single use.

As the optical output/tissue end of the probe is in contact with the tissue of interest, it may be outfitted with various signal enhancing and/or bio-conjugation specific (binding) chemicals, materials, particles (nanoparticles), antibodies, arrays (microarrays), assays, hollow-core photonic crystal fibers, etc. in order to enhance the optical signal and/or provide a molecular, protein, or cellular binding-specific signal (i.e., to confirm the presence and quantify levels of such). Non-limiting examples of signal enhancing and bio-conjugation materials include metallic and/or other material nanoparticles, surface enhanced Raman materials/particles, fluorophores, quantum dots, etc. In the case of signal enhancing materials, the enhancing materials or chemicals on the optical output/tissue end of the probe would come in contact with the tissue and amplify the overall signal of interest (absorption, fluorescence, Raman, etc.) in a non-specific manner (i.e., the entire signal is amplified). For the conjugation/binding materials, these agents at the optical output/tissue end of the probe could be in contact with the tissue of interest and could bind specifically with their counterpart molecule, protein, cell, etc., and produce or amplify the optical signal of interest.

In addition, optical probes as described herein may be used with "optical nose" technology. In such implementations, labels are attached, for example, to an optical output end of an optical probe, the labels specific to a presence of given chemicals. Such technology may be referred to as an extension having a link of a contrast agent and/or a binding agent, and a sensing array of labels may be combined with the optical probes described herein. Hence, in these implementations, a contrast agent may not be used and/or administered, and further such contrast agents would not spill through a surgical cavity.

Alternatively, optical probes as described herein may be used with contrast agents, and systems described herein may be adapted to contrast agents loaded alongside an optical output end of an optical probe. Such contrast agents may be locally deposited alongside one or more optical modalities and delivered locally.

In some implementations, optical probes as described herein may be used with MRI (magnetic resonance imaging) finger-printing that may combine information from multiple optical modalities to search a solution space and determine the type of tissue 203. For example, such implementations may start with some MRI contrast information from pre- and post-operative scanning, and may be used to seed a decision of a tissue type using optical modality data. Similarly, when a type of other local tissue has been confirmed in a patient, such data may be used to seed an initial guess of tissue type of tissue 203

In yet further implementations, optical probes, and/or systems, as described herein may be adapted to cycle through multiple optical interrogations of tissue while iterating through the different types of modalities (including, but not limited to, Raman spectroscopy, mass spectroscopy, Time-of-Flight Fluorescence and the like), with each set of information obtained during each modality informing a next decision.

Furthermore, instead of a specific probe and tool integration design, probes described herein may be mounted on surgical tools using a mounting adaptor attached to the optical probe. The mounting adaptor may be configured for use with a specific surgical tool and/or configured for mounting to various surgical tools. The mounting adaptor may include, but is not limited to a tool mounting sleeve which may be configured for a specific surgical tool and/or mounting location. Both the probe holder and the tool mounting sleeve may be specific to the probe and tool respectively, however the mounting interface may be standard. This allows probes to be mounted on a wide variety of tools and allow flexibility in the location and orientation of the probe placement of the probe on the tool. The standard interface between the probe and the surgical tools means any number of probes may be mounted to a single probe and vice versa.

Probes described herein may be further adapted for use with a surgical navigation system. Either passive or active tracking devices may be mounted on the probe as described above. The position of the optical output/tissue end, including illumination and collection optics, and any stand-off from the tissue relative to the tracking device may be taken into account when recording position of the probe at the tissue. Hence, the position of the tissue being measured may be recorded at the time of measurement via user input indicating a beginning of a measurement and optionally an end of a measurement. The position variation during the measurement process may also be record based on the recorded information acquired from positions of the tracking device, assuming at least a start signal is provided by the user. Given a known volume of interaction for a specific probe and any variations in the probe position, a volume of measurement could be constructed.

Hence, given that the position and volume of the probe measurements may be recorded, these measurement positions and volumes may be registered to pre-operative data sets and/or intra-operative data sets provided that the reference frames of these data sets are spatially calibrated to the tracking system's reference frame. The spatially registered optical measurements may be overlaid on the other data sets and rendered for visualization.

Persons skilled in the art will appreciate that there are yet more alternative implementations and modifications possible, and that the above examples are only illustrations of one or more implementations. The scope, therefore, is only to be limited by the claims appended hereto.

What is claimed is:

1. A device for use with a surgical port used in port-based surgery comprising:
   a surgical tool mounting adaptor comprising a rigid sleeve through which port-based surgical tools are insertable;
   an optical probe;
   a rigid mount removably attaching the optical probe in a fixed position to the surgical tool mounting adaptor,
   the optical probe comprising:
      an optical interface end;
      an optical output end, distal the optical interface end, the optical output end comprising illumination optics and collection optics, the illumination optics configured to illuminate tissue near the optical output end using illumination light from a light source at the optical interface end, the collection optics configured to collect an optical signal from the tissue for multidirectional imaging of the tissue, the optical signal comprising reflecting light from the tissue;
      one or more illumination optical fibers configured to convey the illumination light from the light source to the illumination optics; and,
      one or more collection optical fibers configured to convey the optical signal collected by the collection optics to the optical interface end,
      the illumination optics and the collection optics together comprising common lens sets, each of which are part of the illumination optics and the collection optics, to simultaneously relay the illumination light and collect a portion of the optical signal along a longitudinal axis of the optical probe and at a 90° angle to the longitudinal axis,
      the illumination optics and the collection optics further comprising electromechanical components and micro-electromechanical systems (MEMS) components to move the common lens sets of the illuminations optics and collection optics in order to modify one or more of a focus and a volume of integration thereof, the optical probe being cylindrical and the optical probe comprising a rigid optical probe portion, wherein the optical probe is configured to be disposed within the surgical port and extend lengthwise from the surgical port.

2. The device of claim 1, wherein the optical probe comprises an optical probe sleeve removably holding the rigid optical probe portion.

3. The device of claim 2, wherein the optical probe sleeve is one or more of sterilizable and consumable, the optical probe sleeve further sealing the rigid optical probe portion from the tissue.

4. The device of claim 2, wherein the optical output end is integral with the optical probe sleeve, and the rigid optical probe portion comprises the one or more illumination optical fibers and the one or more collection optical fibers.

5. The device of claim 2, wherein the rigid optical probe portion is sealed inside the optical probe sleeve.

6. The device of claim 1, wherein the respective diameters of each of the optical probe, the illumination optics and the collection optics are 5 mm, and a length of the rigid optical probe portion is 5 cm.

7. The device of claim 1, wherein the optical interface end comprises a connector configured to: connect the one or more illumination optical fibers to the light source; and connect the one or more collection optical fibers to a light analyzer configured to receive and analyze the optical signal from the one or more collection optical fibers.

8. The device of claim 1, wherein the optical output end further comprises a shield configured to one or more of: contact the tissue; and maintain a standoff distance between the tissue and one or more of the illumination optics and the collection optics.

9. The device of claim 1, wherein the illumination optics and the collection optics are configured to modify one or more of: a focal point, a depth of the focal point in the tissue, an illumination spot size, a voxel of the tissue, a numerical aperture of the collection optics, a direction of the illumination light, and a direction of the optical signal collected from the tissue.

10. The device of claim 1, wherein the optical output end comprises one or more materials configured to one or more of: enhance the optical signal from the tissue; and, provide one or more of a molecular protein, and cellular binding-specific signal.

11. The device of claim 10, wherein the materials comprise one or more of: bio-conjugation specific materials, binding materials, antibodies, arrays, microarrays, assays, and hollow-core photonic crystal fibers.

12. The device of claim 1, further comprising a second mount configured to removably attach a tracking device to one or more of the surgical tool mounting adaptor and the optical probe.

13. The device of claim 1, further comprising a second mount configured to removably attach a tracking device of a surgical navigation system to one or more of the surgical tool mounting adaptor and the optical probe.

14. The device of claim 1, wherein the diameter of the optical probe is no more than 5 mm.

* * * * *